United States Patent
Yanagisawa

(10) Patent No.: US 9,006,465 B2
(45) Date of Patent: Apr. 14, 2015

(54) FLUORENE COMPOUND AND PROCESS FOR PREPARING THE SAME

(71) Applicant: Shin-Etsu Chemical Co., Ltd., Tokyo (JP)

(72) Inventor: Hideyoshi Yanagisawa, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/959,198

(22) Filed: Aug. 5, 2013

(65) Prior Publication Data

US 2014/0066636 A1    Mar. 6, 2014

(30) Foreign Application Priority Data

Sep. 4, 2012  (JP) .................. 2012-194355
Jun. 14, 2013  (JP) .................. 2013-125976

(51) Int. Cl.

| | | |
|---|---|---|
| *C07D 301/27* | (2006.01) | |
| *C07D 301/24* | (2006.01) | |
| *C07D 303/12* | (2006.01) | |
| *C07D 303/02* | (2006.01) | |
| *C07F 7/18* | (2006.01) | |
| *C07D 407/12* | (2006.01) | |
| *C07C 39/23* | (2006.01) | |
| *C07F 7/08* | (2006.01) | |

(52) U.S. Cl.
CPC ............ *C07F 7/1876* (2013.01); *C07D 407/12* (2013.01); *C07C 39/23* (2013.01); *C07F 7/0852* (2013.01); *C07C 2103/18* (2013.01)

(58) Field of Classification Search
CPC .... C07D 303/02; C07F 7/0856; C07F 7/0852
USPC ................. 549/215, 514, 518, 554
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 5,354,511 A * | 10/1994 | Wu et al. ............ | 252/582 |
| 6,379,590 B1 * | 4/2002 | Wu et al. ............ | 252/582 |

FOREIGN PATENT DOCUMENTS

JP        B2-4873223        2/2012

* cited by examiner

*Primary Examiner* — Andrew D Kosar
*Assistant Examiner* — Raymond Covington
(74) *Attorney, Agent, or Firm* — Oliff PLC

(57) ABSTRACT

An epoxy group-containing a fluorene compound has a methallyl group at the end thereof and is represented by the following general formula (1):

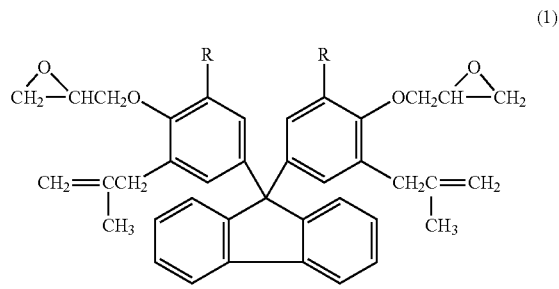

(1)

wherein R represents a hydrogen atom or a methyl group. The compound gives a compound excellent in regioselectivity at the time of hydrosilylation with a Si—H containing organosilicon compound, with a less formed amount of an internally added β adduct, as compared with the conventionally known fluorene compound having an allyl group, so that heat resistance of the resulting organosilicon compound is expected to be improved whereby it is a useful compound.

4 Claims, No Drawings

FLUORENE COMPOUND AND PROCESS FOR PREPARING THE SAME

TECHNICAL FIELD

The present invention relates to a novel fluorene compound having a methallyl group in the molecule.

BACKGROUND ART

As a fluorene compound having both of an allyl group and an epoxy group, a compound represented by the following general formula (X) as disclosed in Patent Literature 1 has been known as a functional epoxy resin. This compound has an allyl group as an unsaturated bond, so that when it is subjected to hydrosilylation with an organosilicon compound having a Si—H bond, regioselectivity of the reaction is poor, and an internally added β adduct is formed. The internally added portion is inferior in heat resistance, so that there is a problem that heat resistance of the compound is poor.

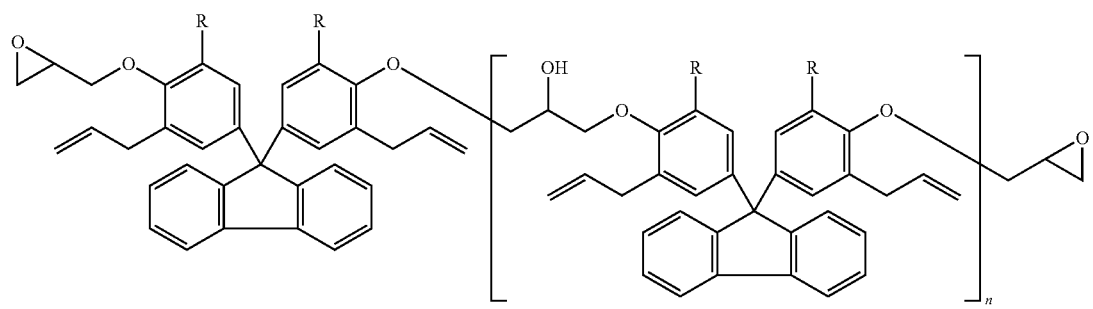

(X)

CITATION LIST

Patent Literature

PATENT LITERATURE 1: JP Patent No. 4873223B

SUMMARY OF THE INVENTION

Technical Problem

The present invention has been accomplished in view of the above-mentioned problems, and an object thereof is to provide a novel fluorene compound having a methallyl group in the molecule which is excellent in regioselectivity at the time of hydrosilylation with a Si—H containing organosilicon compound, which gives a compound with a less formed amount of an internally added β adduct, whereby heat resistance of the organosilicon compound can be improved, and a process for preparing the same.

Solution to Problem

To solve the above-mentioned problems, the present invention is to provide a novel fluorene compound having a methallyl group in the molecule represented by the following general formula (1),

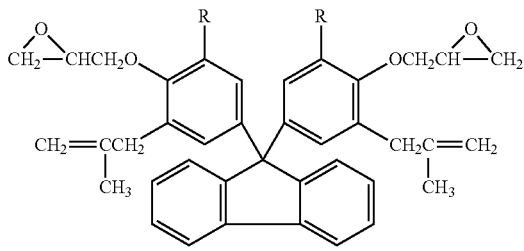

(1)

wherein R represents a hydrogen atom or a methyl group.

Thus, an epoxy group-containing fluorene compound having a methallyl group gives a compound excellent in regioselectivity at the time of hydrosilylation with a Si—H containing organosilicon compound, with a less formed amount of an internally added β adduct.

Also, the present invention is to provide a process for preparing a fluorene compound which is the above-mentioned epoxy group-containing fluorene compound having a methallyl group, comprising reacting at least a fluorene compound having a methallyl group and represented by the following general formula (2), and epichlorohydrin to prepare the compound represented by the following general formula (1),

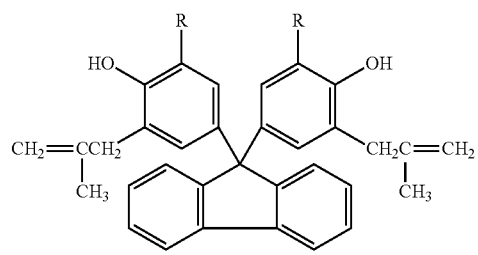

(2)

wherein R represents a hydrogen atom or a methyl group,

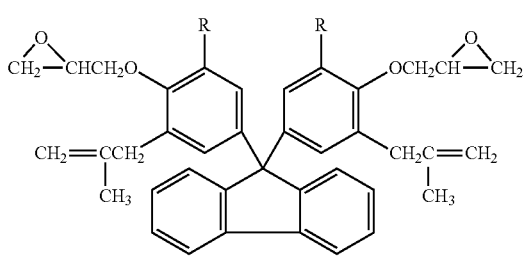

(1)

wherein R represents a hydrogen atom or a methyl group.

According to the above-mentioned preparation process, an epoxy group-containing fluorene compound having a methallyl group which is a novel fluorene compound can be prepared with good yield.

In the present invention, it is also provided a process for preparing a siloxane-introduced fluorene compound, comprising reacting the above-mentioned fluorene compound of the present invention and a Si—H containing organosilicon compound by hydrosilylation in the presence of a catalyst to prepare a siloxane-introduced fluorene compound.

The preparation process mentioned above is preferred since the resulting siloxane-introduced fluorene compound becomes a compound with a less formed amount of an internally added β adduct.

Moreover, in the present invention, it is to provide a fluorene compound having a methallyl group represented by the following general formula (2),

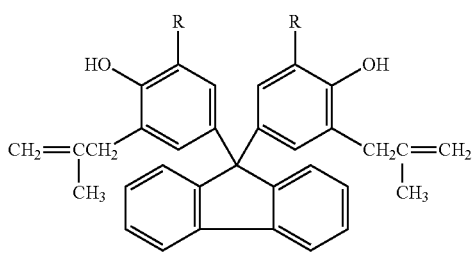

(2)

wherein R represents a hydrogen atom or a methyl group.

When such a fluorene compound having a methallyl group is used, an epoxy group-containing fluorene compound having a methallyl group excellent in regioselectivity can be obtained by subjecting it to hydrosilylation with a Si—H containing organosilicon compound.

Advantageous Effects of Invention

As explained above, an epoxy group-containing fluorene compound having a methallyl group of the present invention is, as compared with the conventionally known fluorene compound having an allyl group, excellent in regioselectivity when it is subjecting to hydrosilylation with a Si—H containing organosilicon compound, and the resulting compound contains a less formed amount of the β adduct internally added thereto. Thus, it is a useful compound since improvement in heat resistance of the resulting organosilicon compound can be expected. The epoxy group-containing fluorene compound having a methallyl group can be prepared according to the preparation process thereof.

DESCRIPTION OF EMBODIMENTS

In the following, the present invention is explained in more detail.

As mentioned above, it has been desired to develop an epoxy group-containing fluorene compound having a methallyl group having excellent regioselectivity when it is subjecting to hydrosilylation with a Si—H containing organosilicon compound, and the resulting compound contains a less formed amount of the β adduct internally added thereto.

Thus, the present inventors have intensively studied to accomplish the above-mentioned objects.

As a result, the present inventors have found that a methallyl group-containing fluorene compound represented by the following general formula (2),

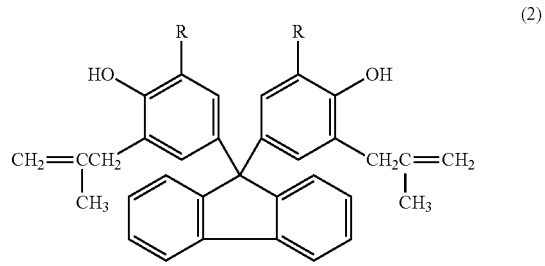

(2)

is prepared and when the compound is reacted with epichlorohydrin, a novel an epoxy group-containing fluorene compound having a methallyl group represented by the following general formula (1),

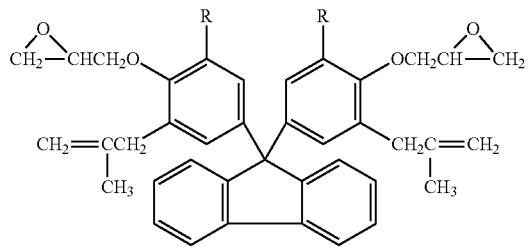

(1)

can be obtained, which compound could be a compound having excellent regioselectivity when it is subjected to hydrosilylation with a Si—H containing organosilicon compound, and containing a less formed amount of the internally added β adduct. Moreover, they have found that the obtained compound can be used for forming an organosilicon compound excellent in heat resistance, water resistance, weather resistance, electric characteristics, etc., whereby the present invention has been accomplished. When an amount of the epichlorohydrin to be used is reduced based on the amount of the compound of the general formula (2), an epoxy group and a phenol group of the compound of the general formula (2) are reacted to form a component having a linkage, but the component does not disturb the present invention.

In the following, the present invention is explained in detail, but the present invention is not limited by these.

The epoxy group-containing fluorene compound having a methallyl group of the present invention is a novel epoxy group-containing fluorene compound having a methallyl group represented by the following general formula (1). In the following general formula (1), R represents a hydrogen atom or a methyl group.

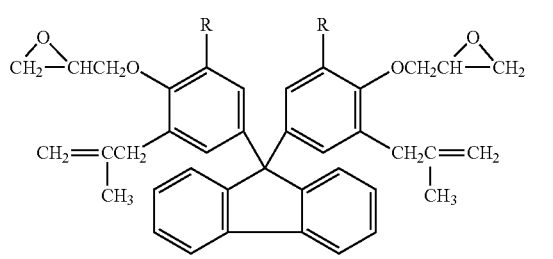

(1)

The compound represented by the general formula (1) may be mentioned the following as representative examples.

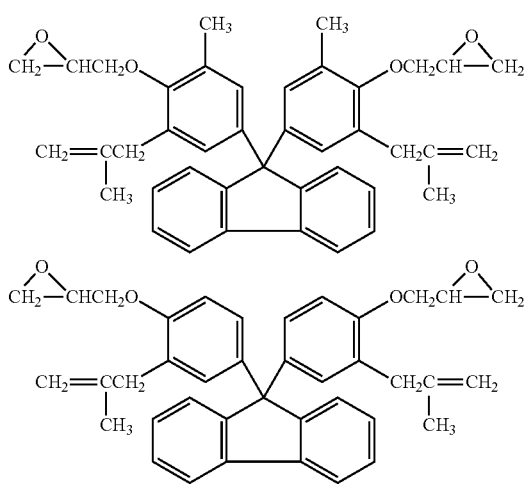

The epoxy group-containing fluorene compound having a methallyl group of the present invention can be obtained by reacting the fluorene compound having a methallyl group represented by the general formula (2) and epichlorohydrin as mentioned above,

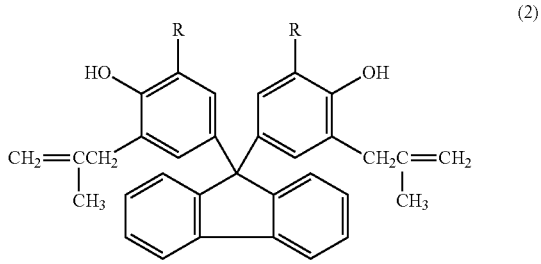

(2)

wherein R represents a hydrogen atom or a methyl group.

The compound represented by the general formula (2) may be mentioned the following as representative examples.

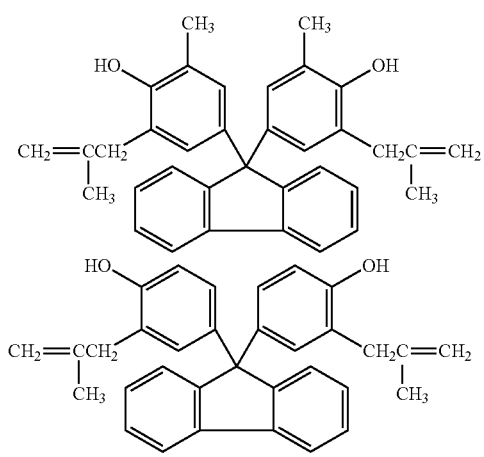

The compound of the general formula (2) can be obtained by reacting 1 mole of the conventionally known 4,4'-(9-fluorenylidene)diphenol with 2 to 10 mole, preferably 2 to 5 mole of a methallyl halide in the presence of a basic compound to prepare a dimethallyl ether of 4,4'-(9-fluorenylidene)diphenol, and the resulting material is subjected to Claisen rearrangement.

The above-mentioned methallyl halide may be used either of methallyl chloride, methallyl bromide or methallyl fluoride, preferably methallyl chloride or methallyl bromide.

The basic compound may be mentioned a metal hydroxide (sodium hydroxide, potassium hydroxide, magnesium hydroxide, etc.), an alkali carbonate (sodium carbonate, potassium carbonate), a metal alkoxide, an ammonium salt, etc. The basic compound is used in an amount of 2 to 10 mole, preferably 2 to 5 mole based on 1 mole of the fluorene compound as a starting material.

The solvent which can be used may be mentioned a conventionally known solvent including an alcohol such as methanol, ethanol, propanol, butanol, etc.; a ketone such as acetone, methyl ethyl ketone, methyl isobutyl ketone, cyclohexanone, etc.; an ether such as diethyl ether, diisopropyl ether, tetrahydrofuran, dioxane, etc.; a nitrile such as acetonitrile, etc.; an aromatic such as benzene, xylene, etc.; an aprotic solvent such as N,N-dimethylformamide, N,N-dimethylsulfoxide, etc. A reaction temperature is 10 to 100° C., and the reaction is carried out for 1 to 100 hours to obtain an etherified product. Then, the obtained etherified product is heated at 30 to 300° C., preferably 50 to 250° C. for 3 to 50 hours to carry out Claisen rearrangement, and the solvent used is removed by distillation to obtain the compound of the general formula (2).

The thus obtained compound of the general formula (2) and epichlorohydrin are reacted to obtain the epoxy group-containing fluorene compound having a methallyl group represented by the general formula (1) of the present invention. Those methods known in this field of the art can be applied to this reaction method.

A reaction temperature of the reaction of the compound of the general formula (2) and epichlorohydrin is optional, and generally carried out at 50 to 120° C., and a reaction time is 3 to 30 hours or so.

A molar ratio the compound of the general formula (2) and epichlorohydrin may be optional, and the compound of the general formula (1) can be obtained by using the epichlorohydrin in excessive amount based on the compound of the general formula (2). If the amount of the compound of the general formula (2) to be used is lowered to the amount of the epichlorohydrin, the epoxy group and the phenol group of the compound of the general formula (2) are reacted to form a component having a linkage, but the component does not disturb the present invention.

An amount of the epichlorohydrin to be used is generally 1.0 to 30 mole, preferably 2.0 to 20 mole, more preferably 3.0 to 15 mole based on 1 mole of the compound of the general formula (2).

In the reaction for obtaining the compound of the general formula (1), use of a catalyst is optional, and an alkali metal hydroxide is generally used. The alkali metal hydroxide may be mentioned sodium hydroxide, potassium hydroxide, etc. The alkali metal hydroxide may be added in the form of a solid material or an aqueous solution. An amount of the alkali metal hydroxide to be used is preferably 0.01 to 0.2 mole based on 1 equivalent of the phenolic hydroxyl group.

When a solid material of the alkali metal hydroxide is used, the material may be used a single kind alone or two or more in combination, and added by dividing into several times or continuously to the reaction system. When an aqueous solution of the alkali metal hydroxide is used, an amount of water accompanied by the aqueous alkali metal hydroxide solution becomes large so that it is necessary to remove water from the reaction system during the reaction.

During the reaction, as the solvent, epichlorohydrin may be used in excessive amount and used as a reaction solvent. Other solvent(s) may be further used optionally, and an aprotic polar solvent is preferably used as a solvent. The aprotic polar solvent may be mentioned dimethylsulfone, dimethylsulfoxide, dimethylformamide, 1,3-dimethyl-2-imidazolidinone, 1,4-dioxane, etc. An amount of the aprotic polar solvent to be used is generally 5 to 200% by weight, preferably 10 to 150% by weight based on the weight of the epichlorohydrin.

During the reaction, a quaternary ammonium salt such as tetramethylammonium chloride, tetramethylammonium bromide, trimethylbenzylammonium chloride, etc., may be used as a catalyst. An amount of the quaternary ammonium salt to be used is generally 0.001 to 0.2 mole, preferably 0.05 to 0.1 mole based on 1 equivalent of the hydroxyl group of the compound of the general formula (2).

These reaction products are washed with water or without washing with water, excess epichlorohydrin or other solvent(s) used, etc., are removed under heating and reduced pressure to obtain the compound of the present invention. In addition, after removing the excess epichlorohydrin or other solvent(s) used, etc., under heating and reduced pressure, the residue is dissolved in a solvent such as toluene, methyl isobutyl ketone, methyl ethyl ketone, etc., and an aqueous alkali metal hydroxide solution of sodium hydroxide, potassium hydroxide, etc., is added to the solution to carry out the reaction again, whereby an epoxy resin with a low total halogen amount can be obtained. After completion of the reaction, by-produced salt is removed by filtration or washing with water, etc., and the solvent such as toluene, methyl isobutyl ketone, methyl ethyl ketone, etc., is removed under heating and reduced pressure to obtain the compound of the present invention.

The compound of the present invention is a novel fluorene compound having a methallyl group and an epoxy group at the end, and can be subjected to hydrosilylation with a Si—H containing organosilicon compound using the methallyl group.

The Si—H containing organosilicon compound is not particularly limited, and may be mentioned a hydrosilane such as trimethoxyhydrosilane, triethoxyhydrosilane, triethylsilane, etc.; a both-ends Si—H containing dimethylpolysiloxane such as 1,1,3,3-tetramethyldisiloxane, α,ω-dihydrodimethylpolysiloxane, α,ω-dihydromethylphenylpolysiloxane, etc.; a one-end Si—H containing dimethylpolysiloxane such as 1,1,3,3,3-pentamethyldisiloxane, 1,1,1,3,3,5,5-heptamethyltrisiloxane, etc.; a side chain Si—H containing dimethylpolysiloxane such as 1,1,1,3,5,5,5-heptamethyltrisiloxane, etc.; a side chain Si—H containing methylphenylpolysiloxane such as 1,1,1,5,5,5-hexamethyl-3-phenyltrisiloxane, etc.; a Si—H containing cyclic polysiloxane such as 2,4,6-trimethylcyclotrisiloxane, 2,4,6,8-tetramethylcyclotetrasiloxane, etc.; a Si—H containing branched polysiloxane, a Si—H containing methylsilicone resin, a Si—H containing methylphenylsilicone resin, a Si—H containing silphenylene compound, a Si—H containing silalkylene compound, etc. When the compound of the present invention and the Si—H containing organosilicon compound are subjected to hydrosilylation, it is possible to co-react with the other vinyl-containing compound(s). Examples of the other vinyl compound(s) may be mentioned a both-ends vinyl-containing dimethylpolysiloxane such as 1,3-divinyl-1,1,3,3-tetramethyldisiloxane, α,ω-divinyldimethylpolysiloxane, α,ω-divinylmethylphenylpolysiloxane, etc.; a side chain vinyl-containing dimethylpolysiloxane such as 1,1,1,3,5,5,5-heptamethyl-3-vinyltrisiloxane, etc.; a side chain vinyl-containing methylvinylphenylpolysiloxane such as 1,1,1,5,5,5-hexamethyl-3-vinyl-3-phenyltrisiloxane, etc.; a vinyl-containing cyclic polysiloxane such as 2,4,6-trimethyl-2,4,6-trivinylcyclotrisiloxane, 2,4,6,8-tetramethyl-2,4,6,8-tetravinylcyclotetrasiloxane, etc.; a vinyl-containing branched polysiloxane; a methylvinylsilicone resin; a methylvinylphenylsilicone resin, etc.

When the hydrosilylation with the Si—H containing organosilicon compound is carried out, a catalyst to be used may be mentioned, for example, a platinum group metal simple substance such as platinum (including platinum black), rhodium, palladium, etc.; a platinum chloride, chloroplatinic acid and chloroplatinate such as $H_2PtCl_4 \cdot xH_2O$, $H_2PtCl_6 \cdot xH_2O$, $NaHPtCl_6 \cdot xH_2O$, $KHPtCl_6 \cdot xH_2O$, $Na_2PtCl_6 \cdot xH_2O$, $K_2PtCl_4 \cdot xH_2O$, $PtCl_4 \cdot xH_2O$, $PtCl_2$, $Na_2HPtCl_4 \cdot xH_2O$ (wherein x is preferably an integer of 0 to 6, particularly preferably 0 or 6.), etc.; an alcohol-modified chloroplatinic acid (U.S. Pat. No. 3,220,972); a complex of chloroplatinic acid and an olefin (U.S. Pat. No. 3,159,601, U.S. Pat. No. 3,159,662 and U.S. Pat. No. 3,775,452); a material in which a platinum group metal such as platinum black, palladium, etc., is carried on a carrier such as alumina, silica, carbon, etc.; a rhodium-olefin complex; chlorotris(triphenylphosphine)rhodium (the so-called Wilkinson's catalyst); a complex of platinum chloride, chloroplatinic acid or chloroplatinate, with a vinyl group-containing siloxane (particularly vinyl group-containing cyclic siloxane), etc. An amount thereof to be used is a catalytic amount, and in general, it is preferably 0.001 to 0.1% by mass as a platinum group metal based on the total amount of the reaction product.

In the above-mentioned hydrosilylation, a solvent may be used, if necessary. The solvent may be mentioned, for example, a hydrocarbon solvent such as a hydrocarbon solvent such as toluene, xylene, hexane, heptane, etc.; an ether solvent such as tetrahydrofuran, dioxane, cyclopentyl methyl ether, etc.; and acetonitrile, etc., and an aromatic hydrocarbon solvent such as toluene, xylene, etc., is preferably used. The above-mentioned reaction conditions are preferably a reaction temperature of, for example, 40 to 150° C., particularly 60 to 120° C. in the viewpoints that the catalyst is not deactivated, and the reaction completes within a short period of time. A reaction time may vary depending on the kind of the reaction product and an amount thereof, and about 0.5 to 100 hours, particularly preferably 0.5 to 30 hours. After completion of the hydrosilylation, the solvent is removed when it is used.

When the compound of the present invention is used, the resulting compound becomes a compound having excellent regioselectivity in the position to which the silicon is bonded, and containing a less formed amount of the internally added β adduct, as compared with the fluorene compound having an allyl group which is conventionally known compound, and improvement in heat resistance of the obtained organosilicon compound can be expected so that it is a useful compound.

EXAMPLES

In the following, the present invention will be explained in more detail by referring to Examples and Comparative Examples, but the present invention is not limited by these.

Synthesis Example 1

In 2 liters of a separable flask equipped with a nitrogen gas introducing tube, a thermometer, a Dimroth condenser and a dropping funnel were charged 175.2 g (0.5 mol) of 4,4'-(9-fluorenylidene)diphenol, 139.6 g (1.01 mol) of potassium carbonate, 108.7 g (1.2 mol) of methallyl chloride and 1000 g of dehydrated acetone, and the mixture was refluxed for 40 hours. After completion, the reaction mixture was filtered and the residue was washed with 800 g of acetone. The filtrate and the washed solution were combined, and acetone was removed by evaporation. To the concentrate was added 1000 g of toluene to dissolve therein, and the solution was washed twice with 1000 g of water. The toluene solution was dried by adding anhydrous sodium sulfate, and toluene was removed by evaporation to obtain 218.4 g of a solid. By subjecting to infrared absorption spectrometry and nuclear magnetic resonance spectrometry, the product was confirmed to be a dimethallyl ether of 4,4'-(9-fluorenylidene)diphenol. The yield was 95.3%. Subsequently, 210 g (0.46 mol) of a dimethallyl ether of 4,4'-(9-fluorenylidene)diphenol was dissolved in 350 g of N,N-diethylaniline and the atmosphere was replaced with nitrogen. The reaction was carried out at a reaction temperature of 150° C. for 20 hours, and the solvent was removed by evaporation under reduced pressure to obtain 205.6 g of a solid. The product was analyzed by infrared absorption spectrometry and $^1$H nuclear magnetic resonance spectrometry and confirmed to be 4,4'-(9-fluorenylidene) dimethallylphenol of the general formula (3).

Example 1

In 2 liters of a separable flask equipped with a nitrogen gas introducing tube, a thermometer, a Dimroth condenser and a dropping funnel, 229 g (0.5 mol) of the compound represented by the following general formula (3) was dissolved in 694 g (7.5 mol) of epichlorohydrin, 1.1 g of tetramethylammonium chloride was further added to the mixture, and the resulting mixture was stirred at 100° C. for 5 hours.

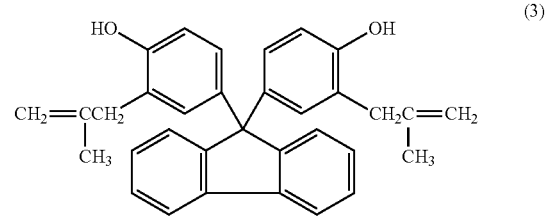

(3)

Next, 110 g of 40% aqueous sodium hydroxide solution was added dropwise to the mixture under reduced pressure (20 kPa) at 70° C. over 3 hours. During the addition, forming water was removed by azeotropic distillation with the epichlorohydrin out of the system, and the evaporated epichlorohydrin was returned into the system. After completion of the dropwise addition, the reaction was further continued for 30 minutes. Thereafter, the formed salt was removed by filtration, washed with water and epichlorohydrin was removed by distillation to obtain 238 g of a colorless solid. This product was analyzed by infrared absorption spectrometry and $^1$H nuclear magnetic resonance spectrometry, and confirmed that the product was an epoxy group-containing fluorene compound having a methallyl group represented by the following general formula (4) of the present invention.

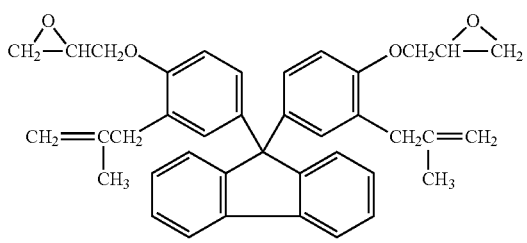

(4)

Example 2

The same reaction as in Example 1 was carried out except that in place of the unsaturated group-containing compound represented by the following structural formula (3),

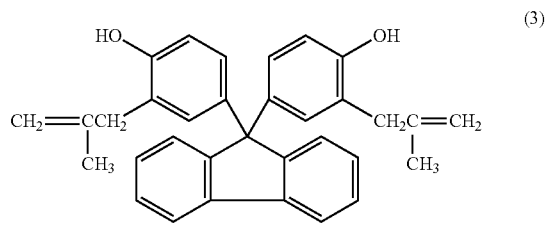

(3)

243 g (0.5 mol) of an unsaturated group-containing compound represented by the following structural formula (5),

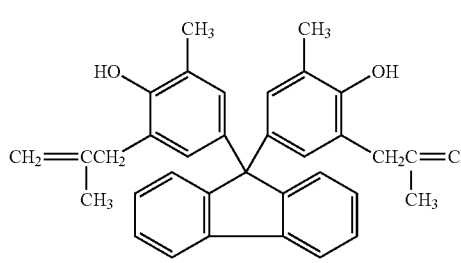

(5)

obtained from 2,2'-dimethyl-4,4'-(9-fluorenylidene)diphenol in the same manner as in Synthesis Example 1 was used and the post-treatment was carried out to obtain 243 g of a colorless solid. This product was analyzed by infrared absorption spectrometry and $^1$H nuclear magnetic resonance spectrometry, and confirmed that the product was an epoxy group-containing fluorene compound having a methallyl group represented by the following general formula (6) of the present invention.

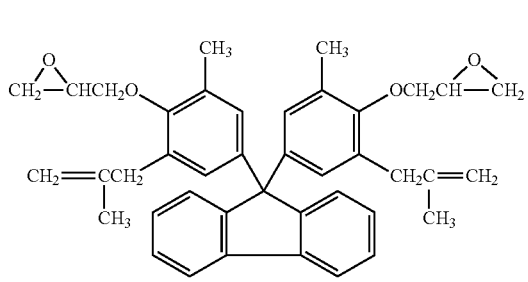

(6)

Synthesis Example 2

In 1 liter of a separable flask equipped with a nitrogen gas introducing tube, a thermometer, a Dimroth condenser and a dropping funnel were charged 143 g (0.25 mol) of an epoxy group-containing fluorene compound having a methallyl group obtained in Example 1 and represented by the following general formula (4),

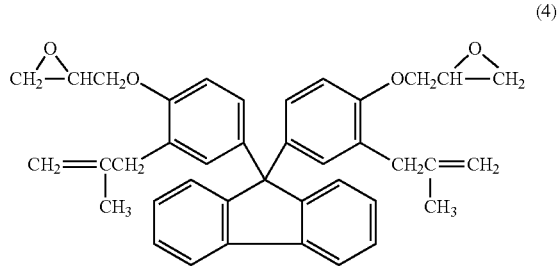

(4)

200 g of toluene, and 0.05 g of tris(1,3-divinyl-1,1,3,3-tetramethyl-disiloxane)-diplatinum(0) (Karstedt catalyst) which contains 2% by weight of platinum, then, to the mixture was gradually added dropwise 74 g (0.5 mol) of pentamethyldisiloxane at 75° C. This dropwise addition required for 30 minutes. After completion of the dropwise addition, the mixture was matured at 75° C. for 5 hours.

After completion of the maturing, the reaction mixture was analyzed by gas chromatography, and confirmed to be a pentamethyldisiloxane remaining amount of 2% or less.

he reaction mixture was concentrated under reduced pressure by a rotary evaporator at 80° C./0.6 kPa, to obtain 210 g of a colorless solid. This product was analyzed by infrared absorption spectrometry and $^1$H nuclear magnetic resonance spectrometry, and confirmed that the product was a fluorene compound into which a siloxane has been incorporated by reacting the methallyl group portion and Si—H, represented by the following structural formula (7),

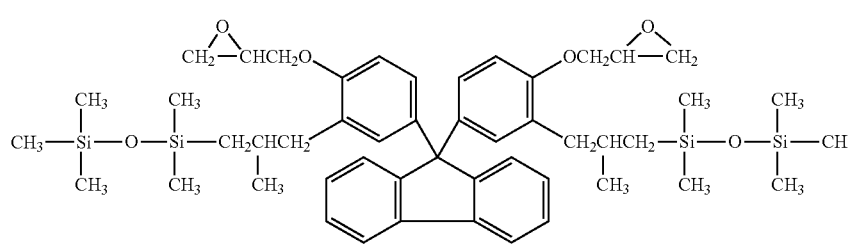

(7)

This product was analyzed by $^1$H nuclear magnetic resonance spectrometry, a purity of the α adduct was 98%, and the isomer (β adduct) represented by the following structural formula (8),

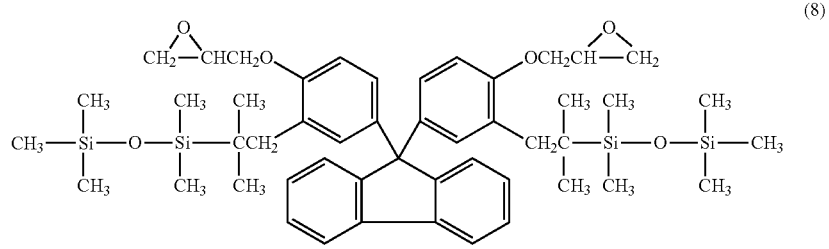
(8)

was confirmed to be formed only by 2%.

Comparative Example 1

The reaction was similarly carried out by using, in place of the compound represented by the following general formula (4),

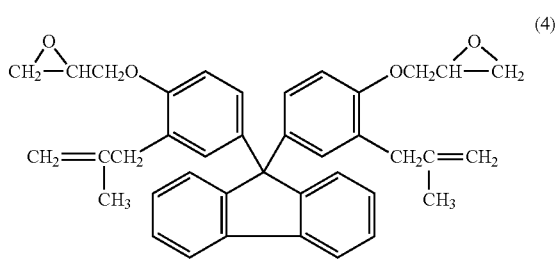
(4)

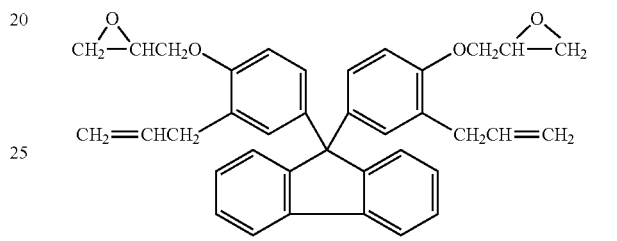
(9)

to obtain 202 g of a colorless solid. The product was analyzed by infrared absorption spectrometry and $^1$H nuclear magnetic resonance spectrometry, and as a result, a fluorene compound into which a siloxane has been introduced by reacting the allyl group portion and Si—H, represented by the following structural formula (10),

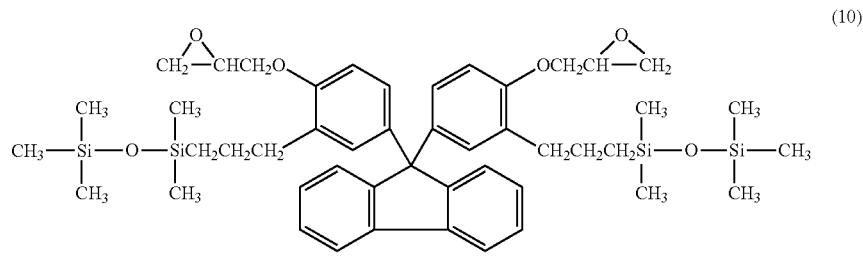
(10)

used in Synthesis Example 2, 136 g (0.25 mol) of an unsaturated group-containing compound represented by the following general formula (9), could be obtained. When the purity of the product was analyzed by $^1$H nuclear magnetic resonance spectrometry, it could be confirmed that the α adduct was 85%, and the remaining about 15% was the β adduct which is an isomer represented by the following structural formula (11).

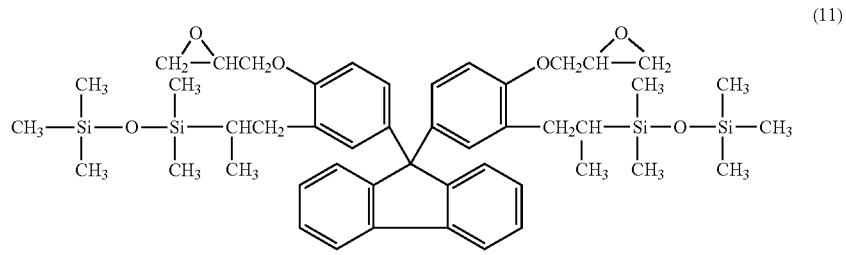

(11)

This is an analysis using the $^1$H nuclear magnetic resonance spectrometry, so that it contains both of a material in which a silicon is added in one end in the molecule (α adduct), and a material in which the other is internally added (β adduct), but such compounds cannot be analyzed or separated. In consideration with the type, the objective compound synthesized in Comparative Example is considered to be less purity.

From the results as mentioned above, it could be demonstrated that the epoxy group-containing fluorene compound having a methallyl group of the present invention gave a compound containing a less formed amount of an internally added β adduct by the hydrosilylation with the Si—H containing organosilicon compound.

That is, such a fluorene compound of the present invention gives a compound in which a formed amount of the internally added β adduct is a little, so that heat resistance of the organosilicon compound is expected to be improved.

It must be stated here that the present invention is not restricted to the embodiments shown by the above-mentioned embodiments. The above-mentioned embodiments are merely examples so that any embodiments composed of substantially the same technical concept as disclosed in the claims of the present invention and expressing a similar effect are included in the technical scope of the present invention.

The invention claimed is:

1. A fluorene compound having a methallyl group and an epoxy group represented by the following formula (1),

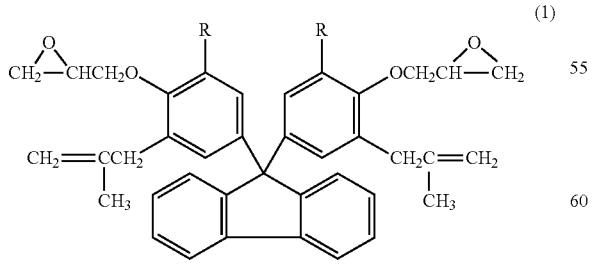

(1)

wherein R represents a hydrogen atom or a methyl group.

2. A process for preparing a fluorene compound represented by the following formula (1),

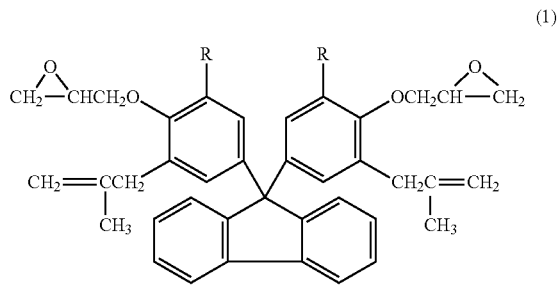

(1)

wherein R represents a hydrogen atom or a methyl group, comprising reacting a fluorene compound having a methallyl group and represented by the following formula (2),

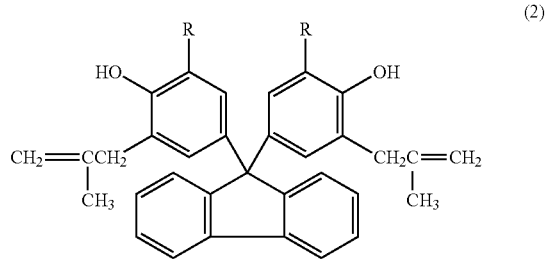

(2)

wherein R represents a hydrogen atom or a methyl group, with epichlorohydrin.

3. A process for preparing a siloxane-introduced fluorene compound, comprising reacting the fluorene compound according to claim 1 and a Si—H containing organosilicon compound by hydrosilylation in the presence of a catalyst to prepare a siloxane-introduced fluorene compound.

4. A fluorene compound having a methallyl group represented by the following formula (2),

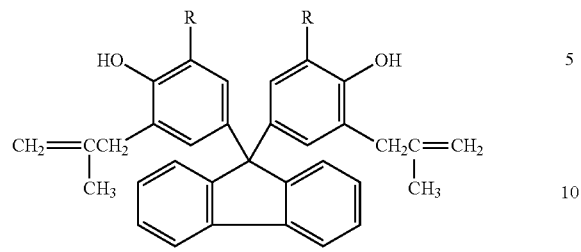
(2)
wherein R represents a hydrogen atom or a methyl group.
* * * * *